United States Patent [19]
Josso et al.

[11] Patent Number: 5,985,925
[45] Date of Patent: Nov. 16, 1999

[54] PHOTOPROTECTIVE/COSMETIC COMPOSITIONS COMPRISING UV-SUNSCREENS/DIALKYL TARTRATES

[75] Inventors: Martin Josso, Paris; Jean-Louis Refregier, Conflans Ste Honorine; Isabelle Hansenne, Paris, all of France

[73] Assignee: Societe L'Oreal S.A., Paris, France

[21] Appl. No.: 09/149,764

[22] Filed: Sep. 9, 1998

[30] Foreign Application Priority Data

Sep. 9, 1997 [FR] France ................................. 97 11173

[51] Int. Cl.$^6$ ................................. A61K 31/19
[52] U.S. Cl. ................ 514/557; 514/557; 514/387; 514/354; 514/246
[58] Field of Search .............. 424/59, 450; 514/557, 514/387, 354, 246; 549/346

[56] References Cited

U.S. PATENT DOCUMENTS

| | | | |
|---|---|---|---|
| 5,609,854 | 3/1997 | Guerrero et al. | 424/59 |
| 5,679,374 | 10/1997 | Fanchon et al. | 454/450 |
| 5,710,177 | 1/1998 | Sauermann et al. | 514/557 |
| 5,733,532 | 3/1998 | Raspanti et al. | 424/59 |
| 5,750,733 | 5/1998 | Vermeer et al. | 549/346 |

FOREIGN PATENT DOCUMENTS

| | | |
|---|---|---|
| 0635260 | 1/1995 | European Pat. Off. . |
| 95/05154 | 2/1995 | WIPO . |
| 96/40047 | 12/1996 | WIPO . |

*Primary Examiner*—Keith D. MacMillan
*Assistant Examiner*—Vickie Kim
*Attorney, Agent, or Firm*—Burns, Doane, Swecker & Mathis, L.L.P.

[57] ABSTRACT

Novel cosmetic/dermatological UV-photoprotective compositions well suited for enhanced PF photoprotection of human skin and/or hair comprise (a) an effective UV-screening amount of at least one benzylidenecamphor sunscreen compound, and/or at least one dibenzoylmethane sunscreen compound, and/or at least one triazine sunscreen compound, and (b) a PF-enhancing amount of at least one dialkyl tartrate, formulated into a topically applicable, cosmetically/dermatologically acceptable vehicle, diluent or carrier therefor.

26 Claims, No Drawings

PHOTOPROTECTIVE/COSMETIC COMPOSITIONS COMPRISING UV-SUNSCREENS/DIALKYL TARTRATES

CROSS-REFERENCE TO PRIORITY APPLICATION

This application claims priority under 35 U.S.C. §119 of FR-97/11173, filed Sep. 9, 1997, assigned to the assignee hereof and hereby expressly incorporated by reference.

BACKGROUND OF THE INVENTION

1. Technical Field of the Invention

The present invention relates to novel cosmetic and/or dermatological compositions for the photoprotection of human skin and/or hair against the damaging effects of UV radiation, in particular solar radiation. More especially, this invention relates to novel cosmetic and/or dermatological compositions comprising at least one UV screening agent of dibenzoylmethane type and/or at least one UV screening agent of the type derived from benzylidenecamphor and/or at least one UV screening agent of the type derived from triazine, these compositions having an improved sun protection factor and which also comprise, in a cosmetically and/or dermatologically acceptable support (vehicle, diluent or carrier) therefor, at least one linear or branched dialkyl tartrate.

2. Description of the Prior Art

It is known to this art that light radiation having wavelengths of between 280 nm and 400 nm permits tanning of the human epidermis, and that light radiation having wavelengths of between 280 and 320 nm, known as UV-B irradiation, causes skin burns and erythema which may be harmful to the development of a natural tan; this UV-B radiation should therefore be screened from the skin.

It is also known to this art that UV-A radiation, having wavelengths of between 320 nm and 400 nm, which causes tanning of the skin, is likely to induce an adverse change therein, especially in the case of sensitive skin or of skin which is continually exposed to solar radiation. UV-A radiation causes, in particular, a loss of elasticity of the skin and the appearance of wrinkles, resulting in premature skin aging. UV-A radiation promotes triggering of the erythemal reaction or amplifies this reaction in certain individuals and may even be the cause of phototoxic or photoallergic reactions. It is thus desirable to also screen UV-A radiation.

Many cosmetic compositions suited for the photoprotection (UV-A and/or UV-B) of the skin are known to this art.

These antisun or sunscreen compositions are commonly in the form of an emulsion of oil-in-water type (namely, a cosmetically acceptable support comprising a continuous aqueous dispersing phase and a discontinuous oily dispersed phase) which contains, in various concentrations, one or more conventional lipophilic and/or hydrophilic organic screening agents which are capable of selectively absorbing harmful UV radiation, these screening agents (and their amounts) being selected as a function of the desired protection factor (the protection factor (PF) being expressed mathematically by the ratio of the irradiation time required to reach the erythema-forming threshold with the UV screening agent to the time required to reach the erythema-forming threshold without UV screening agent).

SUMMARY OF THE INVENTION

After considerable research in the photoprotection arena, it has now surprisingly and unexpectedly been determined that antisun/sunscreen compositions having improved protection factors are provided by admixture of a $C_1$–$C_{16}$ dialkyl tartrate, for example a $C_{12}$–$C_{16}$ dialkyl tartrate, with a photoprotective system including at least one UV screening agent of the type derived from benzylidenecamphor and/or at least one UV screening agent of dibenzoylmethane type and/or at least one UV screening agent of the type derived from triazine, the protection factors in any event being better than those which can be attained with such a photoprotective system alone.

DETAILED DESCRIPTION OF BEST MODE AND SPECIFIC/PREFERRED EMBODIMENTS OF THE INVENTION

More particularly according to the present invention, the phenomenon of enhanced PF is all the more surprising vis-a-vis the prior art, i.e., WO-96/40047, which describes cosmetic or pharmaceutical compositions containing α-hydroxy acid esters, in particular diethyl tartrate, in the presence of conventional UV screening agents, and, more particularly, vis-a-vis EP-A-635,260 which describes antisun/sunsceen lipogels comprising $C_{12}$–$C_{13}$ dialkyl tartrates and UV screening agents of cinnamic or benzophenone type.

Photoprotective compositions based on 2,4,6-tris[p-(2'-ethylhexyl-1'-oxycarbonyl)anilino]-1,3,5-triazine (especially that marketed under the trademark "UVINUL T 150" by BASF) include dialkylesters of α,β-dihydroxylcarboxylic acids only for solubilizing the triazine or for improving the solubilization of this particular UV-screen are also known to this art.

Nonetheless, it has now unexpectedly been determined that protection factors are not improved by means of a dialkyl tartrate in combination with a photoprotective system according to the prior art but not according to the invention, i.e., containing other types of conventional UV screening agents such as cinnamic or benzophenone derivatives.

Thus, the present invention features novel compositions well suited for photoprotecting the skin and/or the hair against ultraviolet radiation, comprising, in a cosmetically acceptable support:

(a) a photoprotective system for screening out UV radiation, which comprised at least one UV screening agent of the type derived from benzylidenecamphor and/or at least one UV screening agent of the type derived from dibenzoylmethane and/or at least one UV screening agent of the type derived from triazine; and (b) a linear or branched dialkyl tartrate preferably having from 1 to 16 carbon atoms in the alkyl moieties thereof.

According to the invention, by the expression "photoprotective system for screening out UV radiation" is intended any compound or any combination of compounds which, by mechanisms which are known per se of absorption and/or of reflection and/or scattering of UV-A and/or UV-B radiation, prevent, or at least limit, the deleterious effects of said radiation upon a surface (skin, hair) onto which this or these compounds have been topically applied. Stated differently, these compounds can be organic photoprotective screening agents which absorb UV radiation or inorganic (nano) pigments which scatter and/or reflect UV radiation, as well as mixtures thereof.

The present invention also features formulating a dialkyl tartrate into a cosmetic or dermatological composition destined to protect the skin and/or the hair against ultraviolet radiation, of the type comprising a photoprotective system for screening out UV radiation, this system comprising at least one UV screening agent of the type derived from benzylidenecamphor and/or at least one UV screening agent of the dibenzoylmethane type and/or at least one UV screening agent of the type derived from triazine, to increase the sun protection factor (SPF) thereof.

This invention also features a cosmetic treatment regime or regimen for protecting the skin and/or the hair against ultraviolet radiation, in particular solar radiation, comprising topically applying thereto an effective amount of one of the subject compositions.

Exemplary dialkyl tartrates are linear compounds whose alkyl moieties are $C_1$–$C_4$ radicals, such as dimethyl, diethyl or dipropyl tartrate. Diethyl tartrate is the preferred.

Dialkyl tartrates in accordance with the present invention which are particularly preferred are those having the following structural formula (A):

$$CH_3-(CH_2)_{\overline{n}}-(R)_{\overline{p}}-CH_2-O-\underset{\underset{H-C-OH}{\underset{H-C-OH}{|}}}{C}=O$$
$$CH_3-(CH_2)_{\overline{n}}-(R)_{\overline{p}}-CH_2-O-C=O$$

(A)

in which R is a radical of formula:

$$-\underset{|}{CH}-\overset{(CH_2)_{\overline{m}}-CH_3}{}$$

p is 0 or 1; n is equal to 12 or 13 when p is equal to 0; and m+n is equal to 8 or 9 when p is equal to 1.

Representative $C_{12}$–$C_{13}$ dialkyl tartrates are more particularly those marketed under the trademark Cosmacol ETI by Enichem Augusta Industriale, as well as the linear $C_{14}$–$C_{15}$ dialkyl tartrates marketed under the trademark Cosmacol ETL by the same company.

The dialkyl tartrates are formulated into the compositions in accordance with the invention at concentrations preferably ranging from 0.1% to 10% by weight relative to the total weight of the composition, and more particularly from 0.2% to 5% by weight.

The dibenzoylmethane derivatives of this invention are compounds per se well known and described, in particular, in FR-A-2,326,405, FR-A-2,440,933 and EP-A-0,114,607, hereby expressly incorporated by reference.

Exemplary dibenzoylmethane derivatives according to the present invention include:

2-Methyldibenzoylmethane,
4-Methyldibenzoylmethane,
4-Isopropyldibenzoylmethane,
4-Tert-butyldibenzoylmethane,
2,4-Dimethyldibenzoylmethane,
2,5-Dimethyldibenzoylmethane,
4,4'-Diisopropyldibenzoylmethane,
4-Tert-butyl-4'-methoxydibenzoylmethane,
2-Methyl-5-isopropyl-4'-methoxydibenzoylmethane,
2-Methyl-5-tert-butyl-4'-methoxydibenzoylmethane,
2,4-Dimethyl-4'-methoxydibenzoylmethane,
2,6-Dimethyl-4-tert-butyl-4'-methoxydibenzoylmethane.

The most particularly preferred dibenzoylmethane compound according to the present invention is 4-tert-butyl-4'-methoxydibenzoylmethane, in particular that marketed under the trademark "Parsol 1789" by Givaudan, this screening agent having the structural formula (I) below:

(I)

Another dibenzoylmethane compound which is preferred according to the present invention is 4-isopropyldibenzoylmethane, this screening agent being marketed under the trademark "Eusolex 8020" by Merck and having the structural formula (II) below:

(II)

Exemplary benzylidenecamphor derivatives according to the present invention include the following compounds:

3-Benzylidenecamphor;
4-Methylbenzylidenecamphor;
3-(4'-Trimethylammonoibenzylidene)camphor methyl sulfate;
Benzylidenecamphorsulfonic acid and salts thereof;
3-(3'-Sulfo-4'-methylbenzylidene)camphor;
Polyacrylamidomethylbenzylidenecamphor.

Also exemplary are the diorganopolysiloxanes containing a benzylidenecamphor functional group, such as those described in EP-B-0,355,777, as well as diorganosiloxanes containing short, linear or cyclic chains or triorganosilanes containing a benzylidenecamphor function, such as those described in EP-B-0,712,855, both also expressly incorporated by reference.

Also representative are benzene-1,4-bis(3-methylidene-10-camphorsulfonic acid) and various salts thereof, described, in particular, in FR-A-2,528,420 and FR-A-2,639,347, which compounds are screening agents that are already per se known (so-called broad-band screening agents) and in fact absorb ultraviolet radiation with wavelengths of between 280 nm and 400 nm, with absorption maxima of between 320 nm and 400 nm, in particular at around 345 nm. These screening agents have the general structural formula (III) below:

(III)

in which B is a hydrogen atom, an alkali metal or, alternatively, a radical $NH(R)_3^+$, wherein the radicals R, which can be identical or different, are each a hydrogen atom, a $C_1$–$C_4$ alkyl or hydroxyalkyl radical or a group $M^{n+}/n$, wherein $M^{n+}$ is a polyvalent metal cation in which n is equal to 2 or 3 or 4, $M^{n+}$ preferably being a metal cation selected from among $Ca^{2+}$, $Zn^{2+}$, $Mg^{2+}$, $Ba^{2+}$, $Al^{3+}$ and $Zr^{4+}$. It will be appreciated that the compounds of formula (III) above include the "cis-trans" isomers around one or more double bond(s) and that all of the isomers are within the scope of the present invention.

4-Methylbenzylidenecamphor is most particularly preferred, this compound being a liposoluble screening agent that is per se known which absorbs in the UV-B range and is marketed, in particular, under the trademark "Eusolex 6300" by Merck, or under the trademark "Parsol 5000" by Givaudan. This compound has the formula (IV) below:

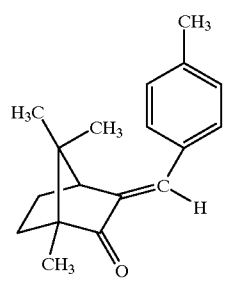

(IV)

2,4,6-Tris[p-(2'-ethylhexyl-1'-oxycarbonyl)anilino]-1,3,5-triazine is the preferred triazine derivative. This screening agent is also per se known, is active in the UV-B range and is in a solid form, which is marketed, in particular, under the trademark "Uvinul T 150" by BASF. This compound has the formula (V) below:

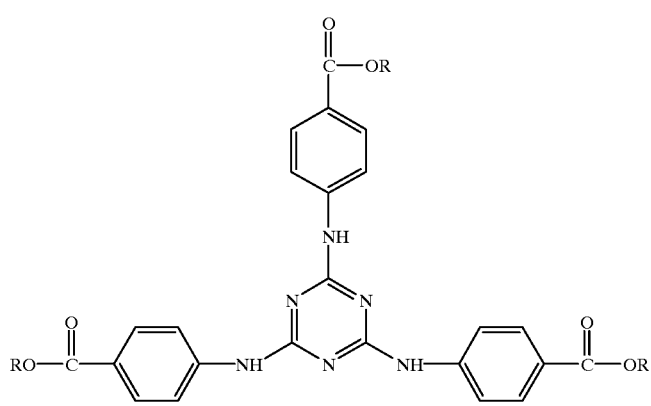

(V)

in which R is a 2-ethylhexyl radical.

Triazine compounds which are also suitable are those described in FR-A-274,472, having the structural formula (VI) below:

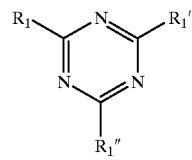

(VI)

in which $R_1$, $R_1'$ and $R_1''$, which may be identical or different, are each a monovalent radical of formula (1) or (2) below:

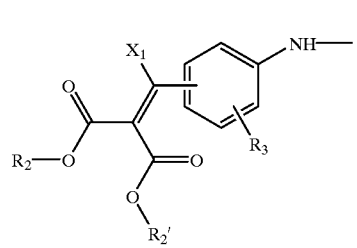

(1)

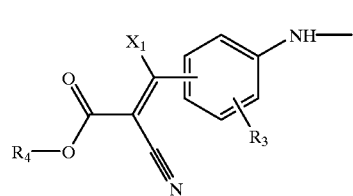

(2)

in which $R_2$ and $R_2'$, which may be identical or different, are each a linear or branched $C_1$–$C_3$ alkyl radical; $R_3$ is a hydrogen atom, a linear or branched $C_1$–$C_4$ alkyl radical, or a $C_1$–$C_4$ alkoxy radical; $R_4$ is a linear or branched $C_1$–$C_{12}$ alkyl radical; and $X_1$ is a hydrogen atom or a phenyl radical optionally substituted with a halogen atom or with a $C_1$–$C_4$ alkyl radical or with a $C_1$–$C_4$ alkoxy radical.

Particularly exemplary compounds of formula (VI) include:
2,4,6-Tris(diethyl 4'-aminobenzalmalonate)-s-triazine;
2,4,6-Tris(diisopropyl 4'-aminobenzalmalonate)-s-triazine;
2,4,6-Tris(dimethyl 4'-aminobenzalmalonate)-s-triazine;

2,4,6-Tris(ethyl α-cyano-4-aminocinnamate)-s-triazine.

The photoprotective compositions according to the invention can also contain either one or more additional organic UV-absorbing screening agents other than benzylidenecamphor derivatives, dibenzoylmethane derivatives or triazine derivatives, or one or more inorganic pigments and/or nanopigments, or, alternatively, mixtures thereof.

The additional organic UV screening agents which are suitable for the antisun/sunscreen compositions in accordance with the invention are conventional hydrophilic or lipophilic screening agents which are active in the UV-A and/or UV-B range. Exemplary of these screening agents, whether alone or in admixture, are 2-phenyl-5-benzimidazolesulfonic acid and salts thereof, cinnamic derivatives, salicylic derivatives, benzophenone derivatives, β,β-diphenylacrylate derivatives, p-aminobenzoic acid derivatives, menthyl anthranilate, and the screening polymers and screening silicones described in WO-93/04665. Other examples of organic screening agents are reported in EP-A-0,487,404.

The photoprotective systems according to the invention are typically present in the subject compositions at a content ranging from 0.1% to 30%, preferably from 0.5 to 15%, by weight relative to the total weight of the composition.

A second category of additional photoprotective active agents which can be formulated into the compositions according to the invention comprises the "pigments." Preferably, these are inorganic nanopigments (average primary particle size: typically ranging from 5 nm to 100 nm, preferably from 10 to 50 nm) of coated or uncoated metal oxides such as, for example, nanopigments of titanium dioxide (amorphous or crystallized in rutile and/or anatase form), iron oxide, zinc oxide, zirconium oxide or cerium oxide, which are all photoprotective agents that are well known per se and which function by physically blocking out (reflection and/or scattering) the UV radiation. Standard coating agents include, moreover, alumina and/or aluminum stearate or, alternatively, silicones. Such coated or uncoated metal oxide nanopigments are described, in particular, in EP-A-0,518,772 and EP-A-0,518,773.

The inorganic (nano)pigment(s) can be present in the compositions according to the invention at a content of from 0.1% to 30%, preferably from 0.5% to 10%, by weight relative to the total weight of the composition.

The other constituents which can be formulated into the subject compositions include, in particular, oils, waxy compounds and cosmetic and/or dermatological active agents, namely, those which are conventional in the cosmetics and/or dermatological fields.

By the term "oil" is intended a compound which is liquid at room temperature. By the term "wax" is intended a compound which is solid or more or less solid at room temperature, and whose melting point is generally greater than 35° C.

Exemplary oils include the mineral oils (petroleum jelly); plant oils (sweet almond oil, macadamia oil, grapeseed oil, jojoba oil); synthetic oils such as perhydrosqualene, fatty alcohols, acids or esters (octyl palmitate, isopropyl lanolate, triglycerides including those of capric/caprylic acids), oxyethylenated or oxypropylenated fatty ethers and esters; silicone oils (cyclomethicone, polydimethylsiloxanes or PDMS) or fluoro oils, and polyalkylenes.

And exemplary waxy compounds include paraffin, carnauba wax, beeswax and hydrogenated castor oil.

The compositions in accordance with the invention can also contain anti-free-radical agents, antioxidants, vitamins such as vitamins E and C, and α-hydroxy acids.

The compositions according to the invention can also contain agents for artificially tanning and/or browning the skin (self-tanning agents) such as, for example, dihydroxyacetone (DHA).

The compositions of this invention can also contain various ingredients, additives and adjuvants conventional in the cosmetics, dermatological or dermopharmaceutical fields, such as dyestuffs, colorants, solvents (water, alcohols, etc.), preservatives, fragrances, moisturizers, pulverulent agents, bactericidal agents and/or odor absorbers, etc.

It will of course be appreciated that one skilled in this art will take care to select the additional complementary compound(s) indicated above and/or the amounts thereof such that the advantageous properties intrinsically associated with the combination [photoprotective system+$C_1$–$C_{16}$ alkyl tartrate] in accordance with the invention are not, or are not substantially, adversely affected by the addition(s) envisaged.

The compositions of the present invention are conveniently formulated via any technique well known to this art, in particular techniques intended for the preparation of dispersions containing an aqueous continuous phase, such as emulsions of oil-in-water type, gels and cream-gels.

The subject compositions are advantageously simple or complex emulsions (O/W, W/O, O/W/o or W/O/W) such as creams or milks, or in the form of a gel or a cream-gel, a powder or a solid tube and can optionally be packaged as an aerosol and can be in the form of a mousse or a spray.

For example, in the antisun or sunscreen formulations in accordance with the invention which have a support of dispersion type containing an aqueous continuous phase, such as oil-in-water emulsions and cream-gels, the aqueous phase (in particular comprising the hydrophilic screening agents) generally constitutes from 50% to 95% by weight, preferably from 70% to 90% by weight, relative to the total weight of the entire formulation, and the oily phase (in particular comprising the lipophilic screening agents) generally constitutes from 5% to 50% by weight, preferably from 10% to 30% by weight, relative to the total weight of the entire formulation.

Preferably, the compositions of this invention are formulated as cream-gels.

In order to further illustrate the present invention and the advantages thereof, the following specific examples are given, it being understood that same are intended only as illustrative and in nowise limitative.

In said examples to follow, all parts and percentages are given by weight relative to the total weight of the composition, unless otherwise indicated.

EXAMPLE 1

A sunscreen formulation A according to the invention was formulated as an emulsion of oil-in-water type and containing:

Phase 1:

| | | |
|---|---|---|
| (a) | 4-(Tert-butyl)-4'-methoxydibenzoylmethane ("Parsol 1789") | 2 g |
| (b) | 2-Ethylhexyl α-cyano-β,β-diphenylacrylate ("Uvinul N 539") | 10 g |
| (c) | 2,4,6-Tris[p-(2'-ethylhexyl-1'-oxycarbonyl)anilino]-1,3,5-triazine ("Uvinul T 150") marketed by BASF | 2 g |
| (d) | Titanium dioxide nanopigment marketed under the trademark "MT100T" by Tayca | 3 g |
| (e) | $C_{14}$–$C_{15}$ Dialkyl tartrate ("Cosmacol ETL") | 1 g |
| (f) | Isohexadecane | 5 g |

-continued

Phase 2:

| | | |
|---|---|---|
| (a) | Polyacrylic acid neutralized with NaOH, marketed under the trademark "PNC 400" by 3V | 0.55 g |
| (b) | Dimethicone copolyol | 0.65 g |

Phase 3:

| | | |
|---|---|---|
| (a) | Benzene-1,4-bis(3-methylidene-10-camphorsulfonic acid) | 1 g |
| (b) | Triethanolamine qs pH 7 | |

Phase 4:

| | | |
|---|---|---|
| (a) | Moisturizers | 4 g |
| (b) | Xanthan gum | 0.5 g |
| (c) | Preservatives | qs |
| (d) | Purified water | qs 100 g |

A comparative antisun or sunscreen formulation A' (not according to the invention), with the same support as that in formulation A but containing no $C_{14}$–$C_{15}$ dialkyl tartrate, was also formulated.

For each of the compositions A and A', the sun protection factor (SPF) was then determined within the UV-A and UV-B radiation range associated therewith. This was determined employing an in vivo technique on five (5) individuals by means of a sun simulator fitted with a Xenon Multiport WG 320 lamp and 6 optical fibers which are placed at skin level. The energy flow was controlled at each irradiation using a 3D-600 model UV-meter.

Each antisun emulsion was applied uniformly with a finger applicator onto the back of each individual, at a rate of 2 mg/cm$^2$, i.e., 0.096 g for an area of 48 cm$^2$.

The irradiation was carried out 15 minutes after each emulsion had been applied. The exposure to UV was carried out for a constant period of time and the irradiation time was selected as a function of the individual's erythema-forming threshold and of the assumed protection factor for each screening composition tested.

The average protection factor (PF) was determined for each screening composition A or A', this protection factor being expressed mathematically by the ratio of the irradiation time required to reach the erythema-forming threshold with the composition to the time required to reach the erythema-forming threshold without the screening composition.

The results obtained are reported in Table I below:

TABLE I

| Composition | A (invention) with dialkyl tartrate | A' (comparative) without dialkyl tartrate |
|---|---|---|
| Average PF (standard deviation) | 30 (3.9) | 15.6 (3.7) |

These results clearly evidence that the addition of a $C_{14}$–$C_{15}$ dialkyl tartrate to a photoprotective system comprising at least one UV screening agent of the type derived from dibenzoylmethane and a UV screening agent of the type derived from benzylidenecamphor significantly increased the photoprotective power thereof.

EXAMPLE 2

A sunscreen formulation B according to the invention was prepared, as an emulsion of oil-in-water type and containing:

Phase 1:

| | | |
|---|---|---|
| (a) | 4-(Tert-butyl)-4'-methoxydibenzoylmethane ("Parsol 1789") | 2.5 g |
| (b) | 2-Ethylhexyl α-cyano-β,β-diphenylacrylate ("Uvinul N 539") | 10 g |
| (c) | $C_{14}$–$C_{15}$ Dialkyl tartrate ("Cosmacol ETL") | 1 g |
| (d) | Stearyl alcohol | 0.5 g |
| (e) | Stearic acid | 1 g |
| (f) | Dimethicone | 1 g |
| (g) | $C_{12}$–$C_{15}$ Alkyl benzoate marketed under the trademark "Finsolv TN" by Finetex | 2 g |
| (h) | Glyceryl stearate/PEG-100 stearate mixture marketed under the trademark Arlacel 165 by ICI | 1.5 g |
| (i) | Triethanolamine | 0.3 g |
| (j) | Preservatives | qs |

Phase 2:

| | | |
|---|---|---|
| (a) | Polyacrylic acid marketed under the trademark "Carbopol 980" by Goodrich | 0.2 g |
| (b) | Triethanolamine | 0.2 g |

Phase 3:

| | | |
|---|---|---|
| (a) | Potassium cetyl phosphate ("Amphisol K" from Givaudan) | 1 g |

Phase 4:

| | | |
|---|---|---|
| (a) | Moisturizers | 15 g |
| (b) | Preservatives | qs |

Phase 5:

| | | |
|---|---|---|
| (a) | Cyclomethicone | 10 g |

Phase 6:

| | | |
|---|---|---|
| (a) | Benzene-1,4-bis(3-methylidene-10-camphorsulfonic acid) | 1 g |
| (b) | Triethanolamine | qs pH 7 |
| (c) | Purified water | qs 100 g |

A comparative sunscreen formulation B', with the same support as that in formulation B but containing no $C_{14}$–$C_{15}$, dialkyl tartrate, was also prepared.

For each of the compositions B and B', the sun protection factor (SPF) associated therewith was then determined.

This was determined via the in vitro technique described by B. L. Diffey et al., in *J. Soc. Cosmet. Chem.*, 40,127–133 (1989); this technique entailed determining the monochromatic protection factors every 5 nm over a wavelength range from 290 to 400 nm and in calculating, from these factors, the sun protection factor according to a given mathematical equation.

The results obtained(average value corresponding to five tests) are reported in Table II below:

TABLE II

| Composition | B (invention) with dialkyl tartrate | B' (comparative) without dialkyl tartrate |
|---|---|---|
| Average SPF (standard deviation) | 37.9 (4.0) | 26.0 (5.6) |

These results clearly evidence that the addition of a $C_{14}$–$C_{15}$, dialkyl tartrate to a photoprotective system comprising at least one UV screening agent of the type derived from dibenzoylmethane and a UV screening agent of the type derived from benzylidenecamphor significantly enhanced the photoprotective power thereof.

EXAMPLE 3

A sunscreen formulation C according to the invention was prepared, in the form of an emulsion of oil-in-water type and containing:

Phase 1:

| | | | |
|---|---|---|---|
| | (a) | 4-(Tert-butyl)-4'-methoxydi-benzoylmethane ("Parsol 1789") | 5 g |
| | (b) | Stearyl alcohol | 0.5 g |
| | (c) | Stearic acid | 1 g |
| | (d) | Dimethicone | 1 g |
| | (e) | $C_{12}$–$C_{13}$ Dialkyl tartrate ("Cosmacol ETI") | 1 g |
| | (f) | $C_{12}$–$C_{15}$ Alkyl benzoate marketed under the trademark "Finsolv TN" by Finetex | 2 g |
| | (g) | Glyceryl stearate/PEG-100 stearate mixture marketed under the trademark Arlacel 165 by ICI | 1.5 g |
| | (h) | Triethanolamine | 0.3 g |
| | (i) | Preservatives | qs |

Phase 2:

| | | | |
|---|---|---|---|
| | (a) | Polyacrylic acid marketed under the trademark "Carbopol 980" by Goodrich | 0.2 g |
| | (b) | Triethanolamine | 0.2 g |

Phase 3:

| | | | |
|---|---|---|---|
| | (a) | Potassium cetyl phosphate ("Amphisol K" from Givaudan) | 1 g |

Phase 4:

| | | | |
|---|---|---|---|
| | (a) | Moisturizers | 15 g |
| | (b) | Preservatives | qs |

Phase 5:

| | | | |
|---|---|---|---|
| | (a) | Cyclomethicone | 10 g |

Phase 6:

| | | | |
|---|---|---|---|
| | (a) | Triethanolamine | qs pH 7 |
| | (b) | Purified water | qs 100 g |

A comparative sunscreen formulation C', with the same support as that in formulation C but containing no $C_{12}$–$C_{13}$ dialkyl tartrate, was then prepared.

For each of the compositions C and C', the sun protection factor (SPF) associated therewith was then determined. This was determined via the technique described in Example 2.

The results obtained (average value corresponding to five tests) are reported in Table III below:

TABLE III

| Composition | C (invention) with dialkyl tartrate | C' (comparative) without dialkyl tartrate |
|---|---|---|
| Average SPF | 7.5 | 3.4 |
| (standard deviation) | (1.1) | (0.4) |

These results clearly evidence that the addition of a $C_{12}$–$C_{13}$ dialkyl tartrate to a photoprotective system comprising a UV screening agent of the type derived from dibenzoylmethane significantly increased the photoprotective power thereof. Equivalent results were obtained using diethyl ($C_2$) tartrate or a $C_{12}$–$C_{13}$ dialkyl tartrate, such as the product Cosmacol ETI instead of the product Cosmacol ETL.

EXAMPLE 4

An antisun formulation D according to the invention was prepared, having the same composition as that of Example 3 but containing, instead of the UV screening agent of the type derived from dibenzoylmethane, 6% by weight of 4-methylbenzylidene-camphor "Eusolex 6300" from Merck and the $C_{14}$–$C_{15}$ product Cosmacol ETL as dialkyl tartrate.

A comparative antisun formulation D', comprising the same support as that in formulation D but containing no dialkyl tartrate, was then prepared.

For each of the compositions D and D', the sun protection factor (SPF) associated therewith was then determined. This was determined via the technique described in Example 2.

The results obtained (average value corresponding to five tests) are reported in Table IV below:

TABLE IV

| Composition | D (invention) with dialkyl tartrate | D' (comparative) without dialkyl tartrate |
|---|---|---|
| Average SPF | 12.4 | 6.5 |
| (standard deviation) | (1.9) | (0.7) |

These results clearly evidence that the addition of a $C_{14}$–$C_{15}$ dialkyl tartrate to a photoprotective system consisting of a UV screening agent of the type derived from benzylidenecamphor significantly increased the photoprotective power thereof. Equivalent results were obtained using diethyl ($C_2$) tartrate or a $C_{12}$–$C_{13}$ dialkyl tartrate such as the product Cosmacol ETI instead of the product Cosmacol ETL.

EXAMPLE 5

An antisun formulation E according to the invention was prepared, having the same composition as that of Example 4 but containing, instead of the UV screening agent of the type derived from benzylidenecamphor, 5% by weight of 2,4,6-tris[p-(2'-ethylhexyl-1'-oxycarbonyl)anilino]-1,3,5-triazine ("Uvinul T 150" marketed by BASF).

A comparative antisun formulation E', with the same support as that in formulation E but containing no dialkyl tartrate, was then prepared.

For each of the compositions E and E', the sun protection factor (SPF) associated therewith was then determined. This was determined via the technique described in Example 2.

The results obtained (average value corresponding to five tests) are reported in Table V below:

TABLE V

| Composition | E (invention) with dialkyl tartrate | E' (comparative) without dialkyl tartrate |
|---|---|---|
| Average SPF | 8.9 | 7.1 |
| (standard deviation) | (0.2) | (0.7) |

These results clearly evidence that the addition of a $C_{14}$–$C_{15}$ dialkyl tartrate to a photoprotective system consisting of a UV screening agent of the type derived from triazine significantly increased the photoprotective power thereof. Equivalent results were obtained using diethyl ($C_2$) tartrate or a $C_{12}$–$C_{13}$ dialkyl tartrate such as the product Cosmacol ETI instead of the product Cosmacol ETL.

EXAMPLE 6 (Comparative)

A sunscreen formulation F (not according to the invention) was prepared, in the form of an emulsion of oil-in-water type having the same composition as that of Example 4 but containing, instead of the UV screening agent of the type derived from benzylidenecamphor, 9% by weight of 2-ethylhexyl p-methoxycinnamate ("Parsol MCX" from Givaudan).

A comparative antisun formulation F', with the same support as that in formulation F but containing no $C_{14}$–$C_{15}$ dialkyl tartrate, was then prepared.

For each of the compositions F and F', the sun protection factor (SPF) associated therewith was then determined. This was determined via the technique described in Example 1.

The results obtained(average value corresponding to five tests) are reported in Table VI below:

TABLE VI

| Composition | F (not according to the invention) with dialkyl tartrate | F' (not according to the invention) without dialkyl tartrate |
| --- | --- | --- |
| Average SPF (standard deviation) | 12.3 (1.1) | 11.6 (2.4) |

These results clearly evidence that the addition of a $C_{14}$–$C_{15}$ dialkyl tartrate to a photoprotective system consisting of a UV screening agent of the type derived from cinnamic acid did not significantly increase the photoprotective power thereof.

EXAMPLE 7 (Comparative)

An antisun formulation G (not according to the invention) was prepared, in the form of an emulsion of oil-in-water type having the same composition as that of Example 4 but containing, instead of the UV screening agent of the type derived from benzylidenecamphor, 6% by weight of 3-benzophenone ("Uvinul M40" from BASF).

A comparative antisun formulation G', with the same support as that in formulation G but containing no $C_{14}$–$C_{15}$ dialkyl tartrate, was then prepared.

For each of the compositions G and G', the sun protection factor (SPF) associated therewith was then determined. This was determined via the technique described in Example 2.

The results obtained(average value corresponding to five tests) are reported in Table VII below:

TABLE VII

| Composition | G (not according to the invention) with dialkyl tartrate | G' (not according to the invention) without dialkyl tartrate |
| --- | --- | --- |
| Average SPF (standard deviation) | 5.4 (1.2) | 6.3 (1) |

These results clearly evidence that the addition of a $C_{12}$–$C_{15}$ dialkyl tartrate to a photoprotective system consisting of a UV screening agent of the benzophenone type did not significantly increase the photoprotective power thereof.

EXAMPLE 8 (Comparative)

An antisun formulation H (not according to the invention) was prepared, in the form of an emulsion of oil-in-water type having the same composition as that of Example 4 but containing, instead of the UV screening agent of the type derived from benzylidenecamphor, 9% by weight of 2-ethylhexyl p-methoxycinnamate ("Parsol MCX" from Givaudan) and 1% by weight of diethyl tartrate instead of the Cosmacol ETL.

A comparative antisun formulation H', with the same support as that in formula H but containing no diethyl tartrate, was then prepared.

For each of the compositions H and H', the sun protection factor (SPF) associated therewith was then determined. This was determined via the technique described in Example 2.

The results obtained(average value corresponding to five tests) are reported in Table VIII below:

TABLE VIII

| Composition | H (not according to the invention) with dialkyl tartrate | H' (not according to the invention) without dialkyl tartrate |
| --- | --- | --- |
| Average SPF (standard deviation) | 11.6 (2.4) | 12.5 (0.9) |

These results clearly evidence that the addition of diethyl tartrate to a photoprotective system consisting of a UV screening agent of the cinnamic type did not increase the photoprotective power thereof.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological UV-photoprotective composition suited for enhanced PF photoprotection of human skin and/or hair, comprising (a) an effective UV-screening amount of at least one benzylidenecamphor sunscreen compound, and/or at least one dibenzoylmethane sunscreen compound, and/or at least one triazine sunscreen compound, and (b) a PF-enhancing amount of at least one dialkyl tartrate, formulated into a topically applicable, cosmetically/dermatologically acceptable vehicle, diluent or carrier therefor.

2. The cosmetic/dermatological UV-photoprotective composition as defined by claim 1, said at least one dialkyl tartrate (b) comprising a $C_1$–$C_{16}$ dialkyl tartrate.

3. The cosmetic/dermatological UV-photoprotective composition as defined by claim 2, said at least one dialkyl tartrate (b) comprising a $C_1$–$C_4$ dialkyl tartrate.

4. The cosmetic/dermatological UV-photoprotective composition as defined by claim 3, said at least one dialkyl tartrate (b) comprising diethyl tartrate.

5. The cosmetic/dermatological UV-photoprotective composition as defined by claim 1, said at least one dialkyl tartrate (b) having the structural formula (A):

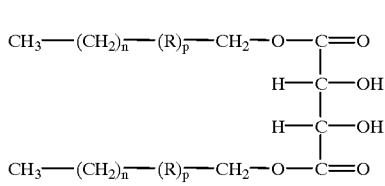

(A)

in which R is a radical of formula:

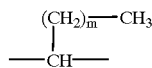

p is 0 or 1; n is equal to 12 or 13 when p is equal to 0; and m+n is equal to 8 or 9 when p is equal to 1.

6. The cosmetic/dermatological UV-photoprotective composition as defined by claim 1, comprising from 0.1% to 10% by weight of said at least one dialkyl tartrate (b).

7. The cosmetic/dermatological UV-photoprotective composition as defined by claim 6, comprising from 0.2% to 5% by weight of said at least one dialkyl tartrate (b).

8. The cosmetic/dermatological UV-photoprotective composition as defined by claim 1, comprising at least one dibenzoylmethane sunscreen compound selected from among 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

9. The cosmetic/dermatological UV-photoprotective composition as defined by claim 8, comprising 4-tert-butyl-4'-methoxydibenzoylmethane.

10. The cosmetic/dermatological UV-photoprotective composition as defined by claim 8, comprising 4-isopropyldibenzoylmethane.

11. The cosmetic/dermatological UV-photoprotective composition as defined by claim 1, comprising at least one benzylidenecamphor sunscreen compound selected from among 3-benzylidenecamphor, 4-methylbenzylidenecamphor, 3-(4'-trimethylammonoibenzylidene)camphor methyl sulfate, benzylidenecamphorsulfonic acid and salts thereof, 3-(3'-sulfo-4'-methylbenzylidene)camphor, and polyacrylamidomethylbenzylidenecamphor.

12. The cosmetic/dermatological UV-photoprotective composition as defined by claim 1, comprising at least one benzylidenecamphor sunscreen compound selected from among a diorganopolysiloxane containing a benzylidenecamphor functional group, a diorganosiloxane which comprises short, linear or cyclic chains and also containing a benzylidenecamphor functional group, and a triorganosilane containing a benzylidenecamphor functional group.

13. The cosmetic/dermatological UV-photoprotective composition as defined by claim 1, comprising at least one benzylidenecamphor sunscreen compound having the structural formula (III):

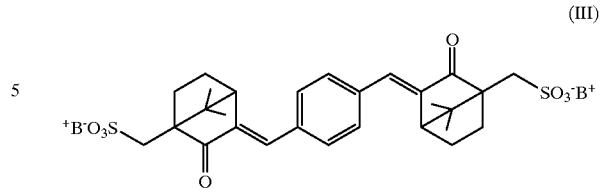

(III)

in which B is a hydrogen atom, an alkali metal or a radical $NH(R)_3^+$, wherein the radicals R, which may be identical or different, are each a hydrogen atom, a $C_1$–$C_4$ alkyl or hydroxyalkyl radical, or a group $M^{n+}/n$, wherein $M^{n+}$ is a polyvalent metal cation and n is equal to 2 or 3 or 4.

14. The cosmetic/dermatological UV-photoprotective composition as defined by claim 13, wherein formula (III) $M^{n+}$ is $Ca^{2+}$, $Zn^{2+}$, $Ba^{2+}$, $Al^{3+}$ or $Zr^{4+}$.

15. The cosmetic/dermatological UV-photoprotective composition as defined by claim 1, comprising 4-methylbenzylidene camphor.

16. The cosmetic/dermatological UV-photoprotective composition as defined by claim 1, comprising at least one triazine sunscreen compound having the structural formula (VI):

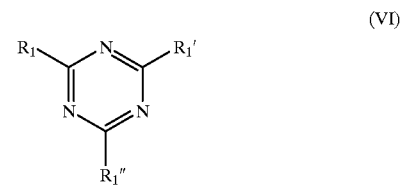

(VI)

in which $R_1$, $R_1'$ and $R_1''$, which may be identical or different, are each a monovalent radical of formula (1) or (2) below:

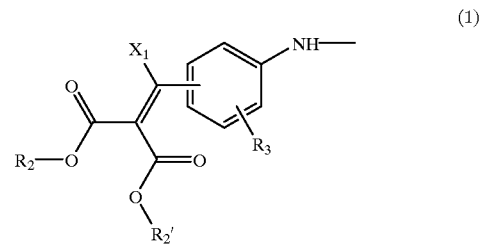

(1)

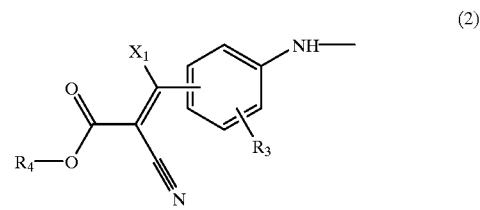

(2)

in which $R_2$ and $R_2'$, which may be identical or different, are each a linear or branched $C_1$–$C_3$ alkyl radical; $R_1$ is a hydrogen atom, a linear or branched $C_1$–$C_4$ alkyl radical or a $C_1$–$C_4$ alkoxy radical; $R_4$ is a linear or branched $C_1$–$C_{12}$ alkyl radical; and $X_1$ is a hydrogen atom or a phenyl radical optionally substituted with a halogen atom or with a $C_1$–$C_4$ alkyl radical or with a $C_1$–$C_4$ alkoxy radical.

17. The cosmetic/dermatological UV-photoprotective composition as defined by claim 16, comprising at least one triazine sunscreen compound selected from among 2,4,6- tris(diethyl 4'-aminobenzalmalonate)-s-triazine, 2,4,6-tris (diisopropyl 4'-aminobenzalmalonate)-s-triazine, 2,4,6-ris (dimethyl 4'-aminobenzalmalonate)-s-riazine, and 2,4,6-tris (ethyl α-cyano-4-aminocinnamate)-s-triazine.

18. The cosmetic/dermatological UV-photoprotective composition as defined by claim 1, comprising at least one triazine sunscreen compound other than 2,4,6-tris[p-(2'-ethylhexyl-1'-oxycarbonyl)anilino]-1,3,5-triazine.

19. The cosmetic/dermatological UV-photoprotective composition as defined by claim 1, further comprising at least one UV-screening active agent other than a benzylidenecamphor, dibenzoylmethane or triazine compound, at least one UV-screening inorganic (nano) pigment, or combination thereof.

20. The cosmetic/dermatological UV-photoprotective composition as defined by claim 19, further comprising at least one UV-screening active agent selected from among 2-phenyl-5-benzimidazolesulfonic acid and salt thereof, cinnamic compound, salicylic compound, benzophenone compound, β,β-diphenylacrylate compound, p-aminobenzoic acid compound, menthyl anthranilate, screening polymer, screening silicone, or combination thereof.

21. The cosmetic/dermatological UV-photoprotective composition as defined by claim 19, further comprising at least one UV-screening titanium oxide, zinc oxide, iron oxide, zirconium oxide or cerium oxide (nano)pigment.

22. The cosmetic/dermatological UV-photoprotective composition as defined by claim 1, further comprising at least one active agent for artificially tanning and/or browning the skin.

23. The cosmetic/dermatological UV-photoprotective composition as defined by claim 1, formulated as a dispersion within a continuous aqueous phase.

24. The cosmetic/dermatological UV-photoprotective composition as defined by claim 1, formulated as an o/w or w/o emulsion.

25. The cosmetic/dermatological UV-photoprotective composition as defined by claim 1, formulated as a cream/gel.

26. A regime or regimen for the UV-photoprotection of human skin and/or hair, comprising topically applying thereto (a) an effective UV-screening amount of at least one benzylidenecamphor sunscreen compound, and/or at least one dibenzoylmethane sunscreen compound, and/or at least one triazine sunscreen compound, and (b) a PF-enhancing amount of at least one dialkyl tartrate, formulated into a topically applicable, cosmetically/dermatologically acceptable vehicle, diluent or carrier therefor.

* * * * *